US012076534B2

(12) United States Patent
Helmer (10) Patent No.: US 12,076,534 B2
(45) Date of Patent: Sep. 3, 2024

(54) MEDICAMENT DELIVERY DEVICE HAVING AN ACTIVATING MECHANISM

(71) Applicant: Sanofi, Paris (FR)

(72) Inventor: Michael Helmer, Frankfurt am Main (DE)

(73) Assignee: Sanofi, Paris (FR)

( * ) Notice: Subject to any disclaimer, the term of this patent is extended or adjusted under 35 U.S.C. 154(b) by 1217 days.

(21) Appl. No.: 16/727,609

(22) Filed: Dec. 26, 2019

(65) Prior Publication Data

US 2020/0129697 A1 Apr. 30, 2020

Related U.S. Application Data

(63) Continuation of application No. 15/309,717, filed as application No. PCT/EP2015/060288 on May 11, 2015, now Pat. No. 10,518,032.

(30) Foreign Application Priority Data

May 12, 2014 (EP) .................................. 14305685

(51) Int. Cl.
*A61M 5/20* (2006.01)
*A61M 5/24* (2006.01)
(Continued)

(52) U.S. Cl.
CPC ........ *A61M 5/2033* (2013.01); *A61M 5/2466* (2013.01); *A61M 5/3202* (2013.01);
(Continued)

(58) Field of Classification Search
CPC .. A61M 5/3202; A61M 5/288; A61M 5/2466; A61M 5/24; A61M 5/2033;
(Continued)

(56) References Cited

U.S. PATENT DOCUMENTS

| 3,401,693 A | 9/1968 | Cohen |
| 3,820,652 A | 6/1974 | Thackston |

(Continued)

FOREIGN PATENT DOCUMENTS

| CN | 102834132 | 12/2012 |
| CN | 102844065 | 12/2012 |

(Continued)

OTHER PUBLICATIONS

International Search Report and Written Opinion in International Application No. PCT/EP2015/060288, dated Aug. 17, 2015, 9 pages.
International Preliminary Report on Patentability in International Application No. PCT/US2015/060288, dated Nov. 15, 2016, 7 pages.

*Primary Examiner* — Kevin C Sirmons
*Assistant Examiner* — Alexandra Lalonde
(74) *Attorney, Agent, or Firm* — Fish & Richardson P.C.

(57) ABSTRACT

The disclosure relates to a medicament delivery device including an activating mechanism, wherein the activating mechanism includes a hollow injection needle, a cartridge containing a dosage of a medicament, a cartridge carrier including at least one resilient arm for holding the cartridge, a removable needle cap for covering the injection needle, and a drive element adapted to couple with the cartridge, wherein the cartridge is retained in a position spaced apart from the injection needle in a proximal direction (P) by the at least one resilient arm when the medicament delivery device is in an initial position (P1), and wherein by removing the needle cap, the cartridge is releasable to be pushed into a distal direction (D) by the drive element with respect to the cartridge carrier.

29 Claims, 6 Drawing Sheets

(51) Int. Cl.
*A61M 5/32* (2006.01)
*A61M 5/34* (2006.01)

(52) U.S. Cl.
CPC ..... *A61M 5/347* (2013.01); *A61M 2005/2013* (2013.01); *A61M 2005/2026* (2013.01); *A61M 2005/247* (2013.01)

(58) Field of Classification Search
CPC .. A61M 5/2429; A61M 5/3204; A61M 5/347; A61M 5/20; A61M 5/28; A61M 5/2455; A61M 5/2459; A61M 5/285; A61M 2005/247; A61M 2005/2073; A61M 2005/2013; A61M 2005/2026; A61M 2005/312; A61M 2005/2474; A61M 5/2422; A61M 5/281; A61M 5/283; A61M 5/286; A61M 5/3213; A61M 5/3216; A61M 5/315; A61M 5/31511; A61M 5/31565; A61M 5/32; A61M 5/3243; A61M 5/3245; A61M 2005/244; A61M 2005/2462; A61M 2005/2477; A61M 2005/2481; A61M 2005/287; A61M 2005/3109; A61M 2005/3118; A61M 2005/3117; A61M 2005/2403; A61M 2005/2407; A61M 2005/2411; A61M 2005/2485
See application file for complete search history.

(56) References Cited

U.S. PATENT DOCUMENTS

| | | | | |
|---|---|---|---|---|
| 4,009,716 | A | * | 3/1977 | Cohen ................... A61M 5/288 604/201 |
| 4,378,015 | A | * | 3/1983 | Wardlaw ............. A61M 5/2033 604/203 |
| 4,957,490 | A | | 9/1990 | Byrne et al. |
| 9,867,944 | B1 | * | 1/2018 | Justus ................. A61M 5/2466 |
| 2004/0267199 | A1 | | 12/2004 | Marshall et al. |
| 2006/0129122 | A1 | | 6/2006 | Wyrick |
| 2010/0274185 | A1 | | 10/2010 | Chun |
| 2012/0179109 | A1 | | 7/2012 | Takemoto et al. |
| 2013/0218093 | A1 | * | 8/2013 | Markussen ........... A61M 5/001 604/198 |
| 2014/0258006 | A1 | | 9/2014 | Baril |

FOREIGN PATENT DOCUMENTS

| | | |
|---|---|---|
| EP | 2554201 | 2/2013 |
| JP | 2012-513264 | 6/2012 |
| JP | 2014-500089 | 1/2014 |
| WO | WO 2010/024975 | 3/2010 |
| WO | WO 2010/072644 | 7/2010 |
| WO | WO 2011/095486 | 8/2011 |
| WO | WO 2011/108575 | 9/2011 |
| WO | WO 2012/073032 | 6/2012 |
| WO | WO 2018/091917 | 5/2018 |

* cited by examiner

MEDICAMENT DELIVERY DEVICE HAVING AN ACTIVATING MECHANISM

CROSS-REFERENCE TO RELATED APPLICATIONS

This application is a continuation of U.S. patent application Ser. No. 15/309,717, filed Nov. 8, 2016, which is a U.S. national stage application under 35 USC § 371 of International Application No. PCT/EP2015/060288, filed on May 11, 2015, which claims priority to European Patent Application No. 14305685.1 filed on May 12, 2014, the entire contents of which are incorporated herein by reference.

TECHNICAL FIELD

The disclosure relates to a medicament delivery device having an activating mechanism.

BACKGROUND

Administering an injection is a process which presents a number of risks and challenges for users and healthcare professionals, both mental and physical. Pre-filled syringes containing a selected dosage of a medicament for administering the medicament to a patient are known in the art. The pre-filled syringes include a hollow injection needle that is in fluid communication with the medicament stored in the cartridge. Due to a long-term storage of the pre-filled syringes, the injection needle can be clogged by the medicament, in particular by a medicament including monoclonal antibodies. A clogged injection needle may lead to an increased injection time.

There remains a need for an improved medicament delivery device having an activating mechanism.

SUMMARY

Some aspects of the disclosure can be implemented to provide an improved medicament delivery device having an activating mechanism.

The object is achieved by a medicament delivery device according to claim 1.

Exemplary embodiments are given in the dependent claims.

In some aspects of the present disclosure, there is provided a medicament delivery device having an activating mechanism, wherein the activating mechanism comprises a hollow injection needle, a cartridge containing a dosage of a medicament, a cartridge carrier comprising at least one resilient arm for holding the cartridge, a removable needle cap for covering the injection needle and a drive element that is adapted to couple with the cartridge. Thereby, the cartridge is retained in a position spaced apart from the injection needle in a proximal direction by the at least one resilient arm when the medicament delivery device is in an initial position, wherein by removing the needle cap, the cartridge is releasable to be pushed into a distal direction by the drive element with respect to the cartridge carrier.

To ensure a counterforce against the prestressing of the drive element, the needle cap is arranged within the medicament delivery device in a manner such that an inner surface of a proximal end of the removable needle cap bears against an outer surface of the at least one resilient arm, wherein an outer surface near the proximal end of the removable needle cap bears against an inner surface of the cartridge carrier.

The provided activating mechanism for the medicament delivery device enables a reliable delivery of the medicament into a patient. The injection needle is formed as a double-ended needle. The injection needle gets in contact with the medicament immediately before the medicament will be ejected. Thus, a risk for a clogged injection needle by the medicament is minimized compared with the related art, whereby an injection time will not be increased. In the related art, the injection needle can be clogged by the medicament stored in the cartridge due to a long-time storage, when the injection needle is in contact with the medicament all the time. With the provided preassembling of the injection needle coupled to the body and spaced apart from the cartridge, the injection needle will keep sterile and clean until the beginning of an injection process. The activating mechanism starts after the needle cap has been removed and thus is very user-friendly. Here, the initial position of the medicament delivery device is a position in which the medicament delivery device would be presented to the user prior to use, whereby the injection needle is not in fluid communication with the medicament stored in the cartridge.

In an exemplary embodiment, the at least one resilient arm is deformed radially outwards when the cartridge is pushed into the distal direction. Thereby, an inner diameter of the cartridge carrier is increased so that the cartridge can pass the area of the cartridge carrier including the at least one resilient arm and move towards the injection needle to get in fluid communication with it. Therefore, the cartridge carrier is made from a resilient material, e. g. a plastic. By the radial outward deformation, the engagement of the cartridge and the at least one resilient arm is released, thus the cartridge is free to move in the distal direction with respect to the cartridge carrier.

In an exemplary embodiment, the drive element is designed as a spring unit that is arranged between a proximal end of the cartridge and a proximal end of the cartridge carrier, wherein the drive element is pre-stressed in the proximal direction when the medicament delivery device is in the initial position and destressed in the distal direction when the needle cap is removed. Hence, the arranged needle cap provides a counterforce against the prestressing force of the drive element. By removing the needle cap, no counterforce acts against the drive element anymore. Thus, the force of the destressing drive element pushes the cartridge into the distal direction.

This implies that the injection needle is allowed to get in fluid communication with the medicament stored in the cartridge, whereby the injection needle pierces a sealing element that is arranged across an open distal end of the cartridge. The sealing element may be designed as a fluid impermeable membrane that seals the medicament and keeps the medicament remaining in the cartridge.

The activating mechanism further comprises a sleeve that is arranged within the outer body and that is movable with respect to the outer body so as to cover or to expose the injection needle. The injection needle is covered by the sleeve when the medicament delivery device is in the initial position, wherein the injection needle is exposed when the medicament delivery device is in an operating position due to a proximal movement of the sleeve with respect to the outer body. The sleeve may be withdrawn after the device is removed from an injection site, e.g., a patient's skin. Thus, the user is prevented from touching and seeing the injection needle before, during and after the injection process. During the injection process, the injection needle is inserted into the injection site, whereby the sleeve abuts against the injection site.

Moreover, the activating mechanism comprises a bung that is disposed within the cartridge for proximally limiting the cartridge when the medicament delivery device is in the initial position. The activating mechanism further comprises a piston rod that is adapted to engage the bung for displacing it within the cartridge. The bung seals the cartridge proximally, whereby the displacement of the bung within the cartridge, in particular in the distal direction, is realized by a force of the piston rod. The piston rod may replace the spring unit as the drive element pushing the cartridge in the distal direction after the needle cap has been removed. Therefore, the piston rod may be coupled to a button for an automatic medicament delivery or a manual force will be applied on the piston rod.

Further, there is provided a medicament delivery device comprising an activating mechanism as it is described before.

In an exemplary embodiment, to ensure an assembly capability from one direction during a final assembly process, the drive element is coupled to the cartridge carrier by a bayonet socket that ensures a releasable and reliable connection between the drive element and the cartridge carrier. In addition, this enables an easy assembly of the drive element within the medicament delivery device.

In a further exemplary embodiment, the at least one resilient arm is designed as a lug-shaped cut out comprising a first section based on a circumference of the cartridge carrier and protruding radially inwards, and a hook-shaped second section protruding axially in the distal direction, wherein the free hook end of the second section protrudes radially inwards. The resilient arm retains the cartridge in position as long as the needle cap is not removed. There may be arranged one or more resilient arms around the circumference of the cartridge carrier, thus the cartridge is reliably held in position. Thereby, a shoulder of the cartridge bears against the hook end of the second section as long as the drive element is prestressed in the proximal direction.

Furthermore, there is provided a medicament delivery device comprising the activating mechanism as it is described before. The medicament delivery device is suitable for use with a manual needle insertion and a manual medicament delivery as well as for use with an automatic needle insertion and/or an automatic medicament delivery. Particularly, the medicament delivery device is suitable for use in autoinjectors that are sleeve- or button-triggered, in particular sequence independently button-triggered. For button-triggered devices, a powerpack design has to ensure that the piercing of the injection site will start when a needle safety mechanism is activated.

In an exemplary embodiment, a transversal opening is arranged through the cartridge carrier, wherein a sealing part is arrangeable within the opening distally from the cartridge and proximally from the inner needle section. In an initial position, the sealing part is located within the opening distally from the cartridge, e.g. distally from a sealing element of the cartridge and proximally from the inner needle section and from a needle hub. Due to the sealing part being arranged within the opening, the cartridge cannot be advanced prior to removal of the sealing part. The cartridge is thus retained in a position spaced apart from the injection needle in the proximal direction by an additional safety feature, i.e. the sealing element, which has to be removed for rendering the medicament delivery device operable.

In an exemplary embodiment, the opening is further arranged through the needle cap. The needle cap can thus not be removed prior to removal of the sealing part such that the user is encouraged to comply with a sequence of operations in order to maintain the needle sterile, wherein the sealing part has to be removed in order to allow removal of the needle cap.

In an exemplary embodiment, the opening is further arranged through the outer body and/or through the sleeve. Thus, the sealing part additionally prevents depression of the sleeve prior to removal of the sealing part further improving user compliance.

In an exemplary embodiment, the sealing part is connected by a flexible strip to the cap. This may improve the user's understanding that the sealing part and the cap are safety features which both have to be removed for rendering the medicament delivery device operable. In an exemplary embodiment, the cap and the sealing part are integrally shaped with the flexible strip.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given hereinbelow and the accompanying drawings which are given by way of illustration only, and thus, are not limitive of the present disclosure, and wherein.

Corresponding parts are marked with the same reference symbols in all figures.

DETAILED DESCRIPTION

In the present application, when the term "proximal section/end" is used, this refers to the section/end of the medicament delivery device, or the sections/ends of the components thereof, which under use of the medicament delivery device is located the furthest away from the medicament delivery site of the patient. Correspondingly, when the term "distal section/end" is used, this refers to the section/end of the medicament delivery device, or the sections/ends of the components thereof, which under use of the medicament delivery device is located closest to the medicament delivery site of the patient.

By way of illustration, a cartesian coordinate system with the coordinates x, y and z is illustrated in all FIGS. 1 to 4.

Figure 1:
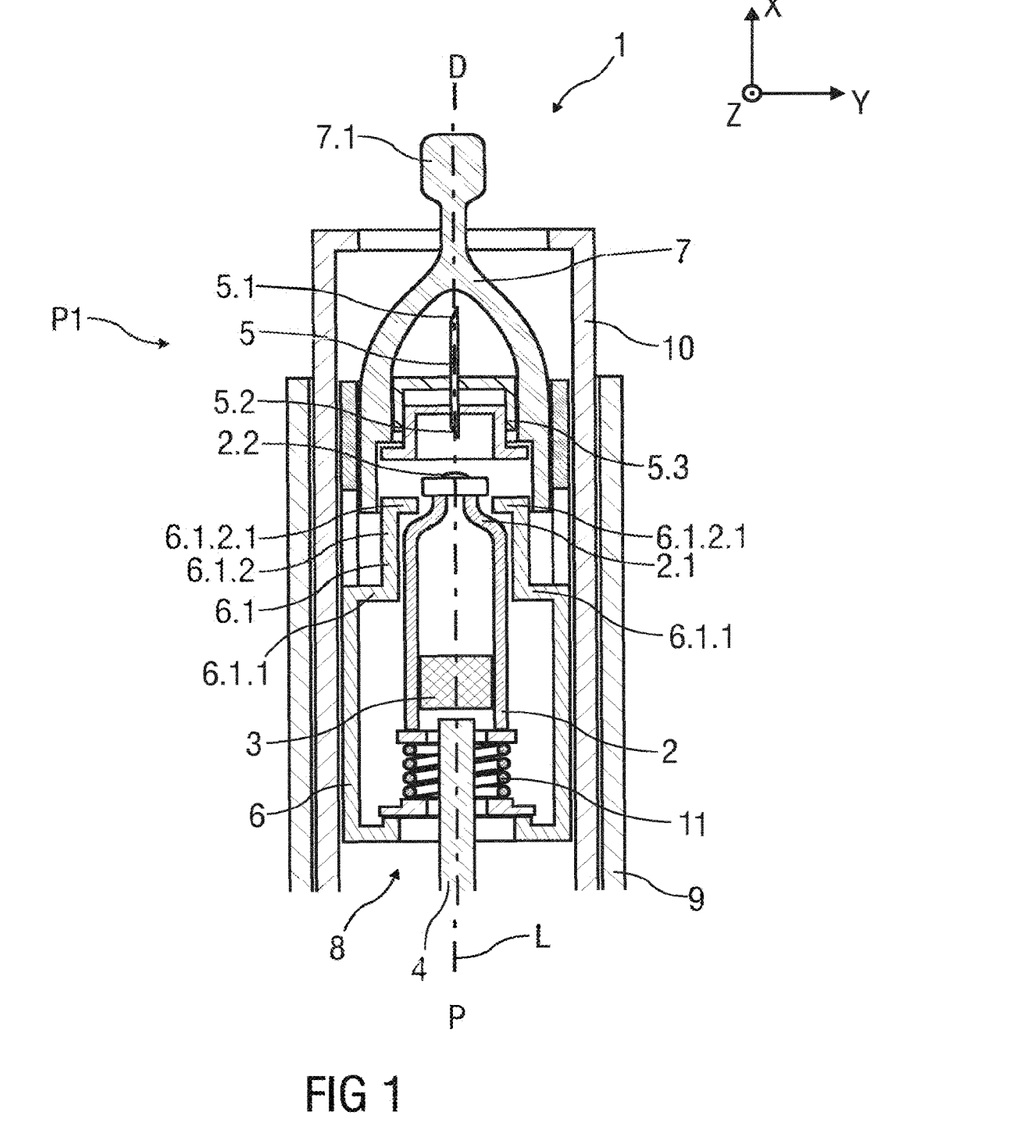
FIG. 1 is a schematic longitudinal section view of an exemplary embodiment of a medicament delivery device in an initial position.

FIG. 1 shows a schematic longitudinal section view of an exemplary embodiment of a medicament delivery device 1, whereby the medicament delivery device 1 is in an initial position P1. Thereby, the medicament delivery device 1 would be presented to a user prior to use.

The medicament delivery device 1 comprises a cartridge 2 forming a cavity that contains a selected dosage of a medicament. The cartridge 2 comprises a cylindrically shaped main body and a neck section on a distal end of the main body, whereby a shoulder 2.1 connects the main body and the neck section. The distal end of the cartridge 2 includes a flange to retain a sealing element 2.2, e. g. a fluid impermeable membrane or foil, which is arranged across the open distal end of the cartridge 2. The sealing element 2.2 seals the medicament distally against environmental influences and ensures that the medicament remains within the cartridge 2. The cartridge 2 is proximally limited by a bung 3 that is disposed within the cartridge 2 on a proximal end when the medicament delivery device 1 is in the initial position P1. The bung 3 is arranged spaced from a piston rod 4, whereby the bung 3 is engageable with the piston rod 4. The piston rod 4 is adapted to displace the bung 3 within the cartridge 2 for ejecting the medicament from the cavity through an injection needle 5 that is arranged spaced from the cartridge 2 along a longitudinal axis L in a distal direction D when the medicament delivery device 1 is in the initial position P1. In context of the present application, the injection needle 5 is suitable for intramuscular, subcutaneous, intradermal or transcutaneous injections with corresponding lengths.

The cartridge carrier 6 comprises a hollow main body for receiving the cartridge 2. An inner diameter of the cartridge carrier 6 is significantly greater than an outer diameter of the cartridge 2. For holding the cartridge 2, the cartridge carrier 6 comprises two resilient arms 6.1 that retain the cartridge 2 in position before injection, in particular in the initial position P1 or initial state of the medicament delivery device 1. While the exemplary embodiment depicts only two resilient arms 6.1, those of skill in the art will understand that more than two resilient arms 6.1 may be utilized.

Respectively, the resilient arms 6.1 are designed as lug-shaped cut outs divided in a first section 6.1.1 and a second section 6.1.2. The first section 6.1.1 is based on the circumference of the cartridge carrier 6 and protrudes in a radial inward direction. The second section 6.1.2 follows the first section 6.1.1 in a rectangular angle, thus protruding in the distal direction D. The second section 6.1.2 comprises a hook-shaped free end 6.1.2.1, whereby the hook end 6.1.2.1 protrudes in the radial inward direction. The cartridge carrier 6 is made from a resilient material, e. g. a plastic, to enable a radially outward deforming of the resilient arms 6.1.

An internal diameter of the cartridge carrier 6 in the area of the resilient arms 6.1 is smaller than the outer diameter of the cartridge 2. Thus, the cartridge 2 is held in the cartridge carrier 6 in a manner that the shoulder 2.1 of the cartridge 2 abuts against the hook ends 6.1.2.1 of the resilient arms 6.1. A movement of the cartridge 2 in the distal direction with respect to the cartridge carrier 6 is prevented by the resilient arms 6.1.

To prevent a deformation of the resilient arms 6.1 when the medicament delivery device 1 is in the initial position P1, a removable needle cap 7 is provided that covers and seals an outer needle section 5.1 of the injection needle 5 and that is arranged in a manner that a proximal end of the removable needle cap 7 bears against an outer surface of the resilient arms 6.1, whereby an outer surface near the proximal end of the removable needle cap 7 bears against an inner surface of the cartridge carrier 6 that is located near a distal end of the cartridge carrier 6. In particular, a proximal section of the needle cap 7 is arranged between the resilient arms 6.1 and the inner surface of the cartridge carrier 6 relating to a radial direction. Thus, the resilient arms 6.1 cannot be deformed radially outwards in recesses built by the cut out of the resilient arms 6.1 if the cartridge 2 would be free to move in the distal direction D with respect to the cartridge carrier 6.

To ensure a desired deformation of the resilient arms 6.1 after the needle cap 7 is removed, the medicament delivery device 1 comprises a drive element 8 that is arranged between a proximal end of the cartridge 2 and a proximal end of the cartridge carrier 6. In the present embodiment, the drive element 8 is designed as a coil spring unit 11 that is coupled with its proximal end to the cartridge carrier 6 by a bayonet socket. Alternatively, the spring unit 11 may be coupled to the cartridge carrier 6 by any other suitable connection.

A distal end of the spring unit 11 is arranged on the proximal end of the cartridge 2, whereby the spring unit 11 is prestressed in the proximal direction P.

The needle cap 7 provides a counterforce against the prestressing of the spring unit 11. In particular, by removing the needle cap 7, the spring unit 11 is released and destresses into the distal direction D. Thereby, the cartridge 2 is pushed in the distal direction D against the resilient arms 6.1 by the destressed spring unit 11, whereby the resilient arms 6.1 are free to move radially outwards, because the needle cap 7 does not bear against the resilient arms 6.1 anymore.

The distal movement of the cartridge 2 enables the injection needle 5 to get in fluid communication with the medicament stored in the cartridge 2.

Thereby, the injection needle 5 comprises the outer needle section 5.1 and an inner needle section 5.2 that is targeted inside the cartridge carrier 6 directed to and distally spaced from the sealing element 2.2 of the cartridge 2, when the medicament delivery device 1 is in the initial position P1. The injection needle 5 is coupled to a substantially elongate and cylindrical outer body 9 by a needle thread 5.3 that provides a luer-lock connection to the outer body 9. Alternatively, the injection needle 5 may be coupled to the outer body 9 by any other suitable connection.

The outer body 9 centres the cartridge carrier 6 and a sleeve 10 within the outer body 9. The cartridge carrier 6 is rigidly connected to the outer body 9, wherein the sleeve 10 is slidably coupled to the outer body 9 for allowing relative movement in the distal direction D and/or the proximal direction P so as to cover or to expose the injection needle 5. The axial translation of the sleeve 10 corresponds with an insertion depth of the injection needle 5 at least. In the present application, the axial translation of the sleeve 10 is greater than the insertion depth of the injection needle 5.

Figure 2:
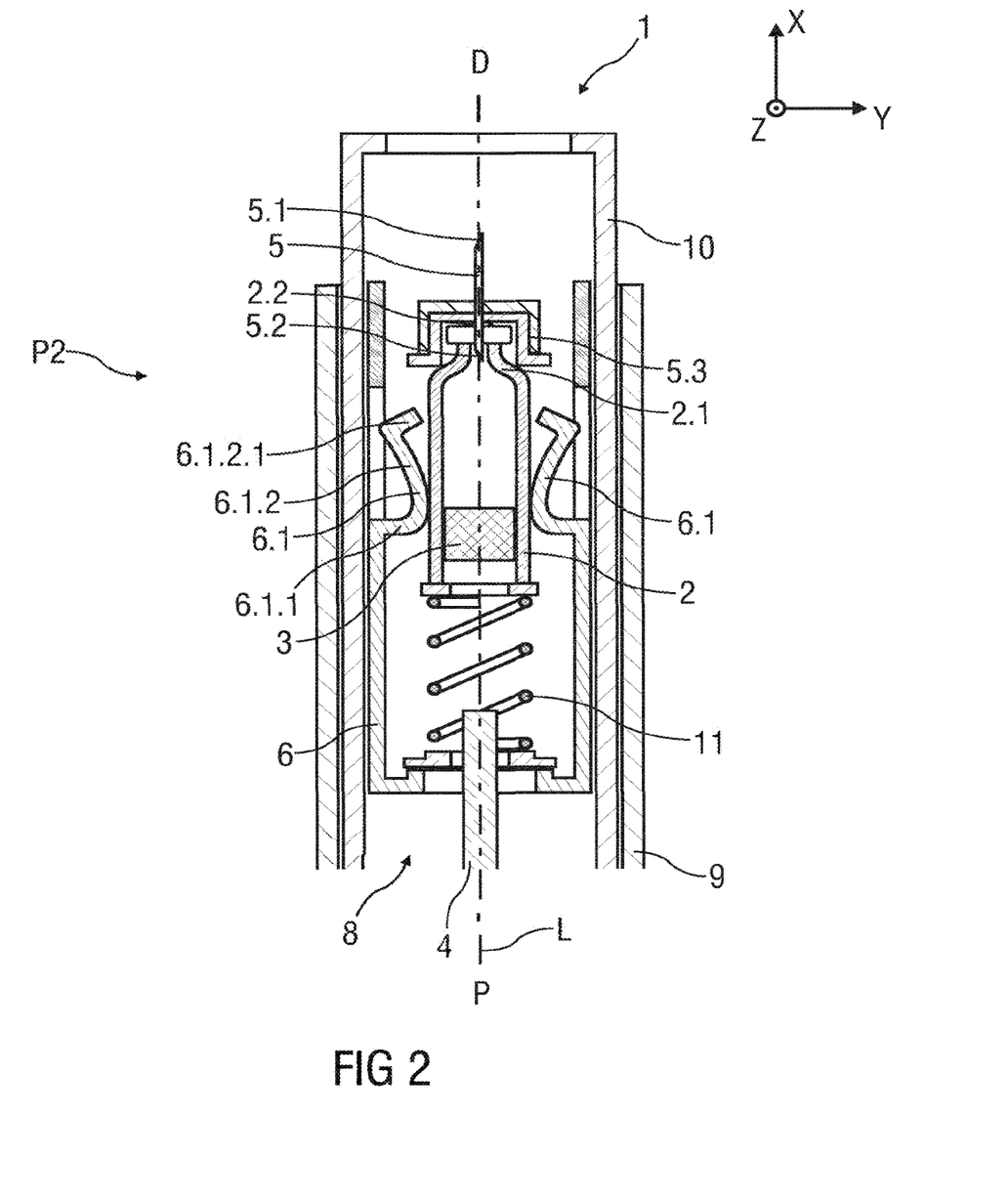
FIG. 2 is a schematic longitudinal section view of an exemplary embodiment of a medicament delivery device in an operating position.

FIG. 2 shows a schematic longitudinal section view of an exemplary embodiment of the medicament delivery device 1, whereby the medicament delivery device 1 is in an operating position P2. Thereby, the injection needle 5 is in contact with the medicament and the injection needle 5 is still covered by the sleeve 10.

In order to perform the injection process, the medicament delivery device 1 may be operated according to the following exemplary method.

The needle cap 7 is removed from the injection needle 5 by pulling off the needle cap 7 with the help of a removal aid 7.1. At this time, the injection needle 5 is still covered by the sleeve 10 preventing a user from touching and seeing it.

After removing the needle cap 7, the spring unit 11 distresses and pushes the cartridge 2 in the distal direction D against the resilient arms 6.1. The resilient arms 6.1 deform radially outwards into the recesses of the cartridge carrier 6. Thus, the cartridge 2 moves in the distal direction D with respect to the cartridge carrier 6 and the sleeve 10 until it abuts against the needle thread 5.3, whereby the needle tip of the inner needle section 5.2 pierces the sealing element 2.2 of the cartridge 2. Now, the injection needle 5 is in fluid communication with the medicament, but still covered by the sleeve 10 as it is shown in FIG. 2.

The medicament delivery device 1 may be held at the outer body 9 and the sleeve 10 is pushed against an injection site, e.g. a patient's skin. Consequently, the sleeve 10 moves in the proximal direction P with respect to the outer body 9 and the cartridge 2 against a force of a not shown spring, by which the sleeve 10 is supported.

The cartridge 2 and the injection needle 5 stay in position relative to the outer body 9 while the sleeve 10 moves in the proximal direction P. Hence, the injection needle 5 is exposed and inserted into the injection site. Once the relative movement of the sleeve 10 stops, the injection needle 5 has reached its insertion depth. By pushing the piston rod 4 in the distal direction D, the bung 3 is displaced within the cartridge 2 and the medicament is ejected through the injection needle 5 into the injection site. Alternatively, the medicament delivery device 1 may be button-triggered.

In the illustrated embodiments, the medicament delivery device 1 may be provided with manual needle insertion and manual medicament delivery. Likewise, the medicament delivery device 1 could be provided with automatic needle insertion and/or automatic medicament delivery in order to adjust the injection force. With regard to the latter, the medicament delivery device 1 may be provided as a modular unit that is connectable to an autoinjector device. To ensure sterility, the modular unit may be provided with a blistering. Alternatively, the needle cap 7 and the cartridge carrier 6 are designed in such a manner that a compartment to the inner needle section 5.2 is sterile sealed against the components of the medicament delivery device 1 near the inner needle section 5.2.

Referring to an exemplary embodiment, there is provided an audible feedback when the injection process is completed. The audible feedback may be generated by the spring unit 11 in the form of a clicking or snapping sound. This can be performed by support of the piston rod 4 that lifts and releases the spring unit 11, if a proximal end of the piston rod 4 reaches an end position. Consequently, a clicking sound will occur.

Figure 3:
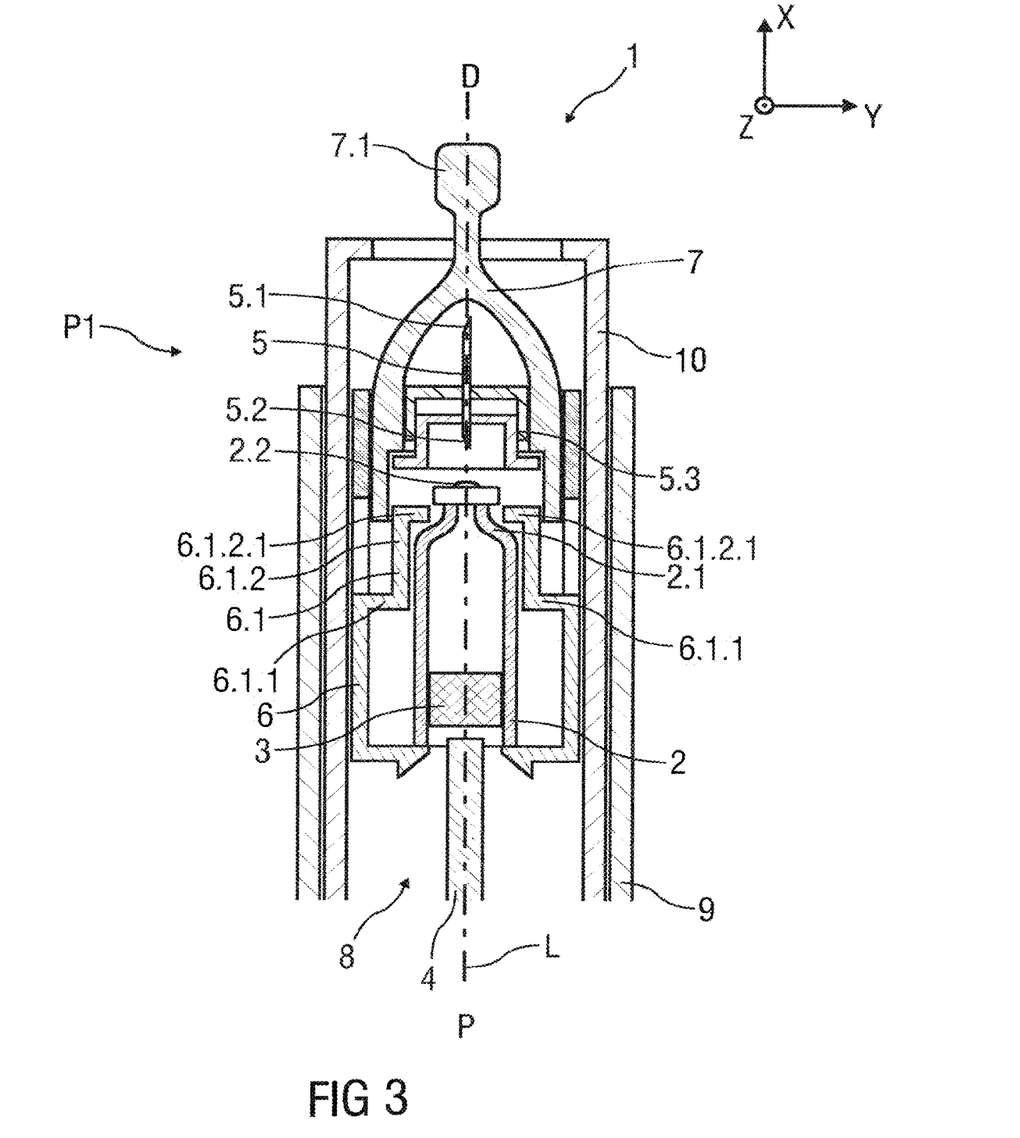
FIG. 3 is a schematic longitudinal section view of an alternative embodiment of a medicament delivery device in an initial position.
Figure 4:
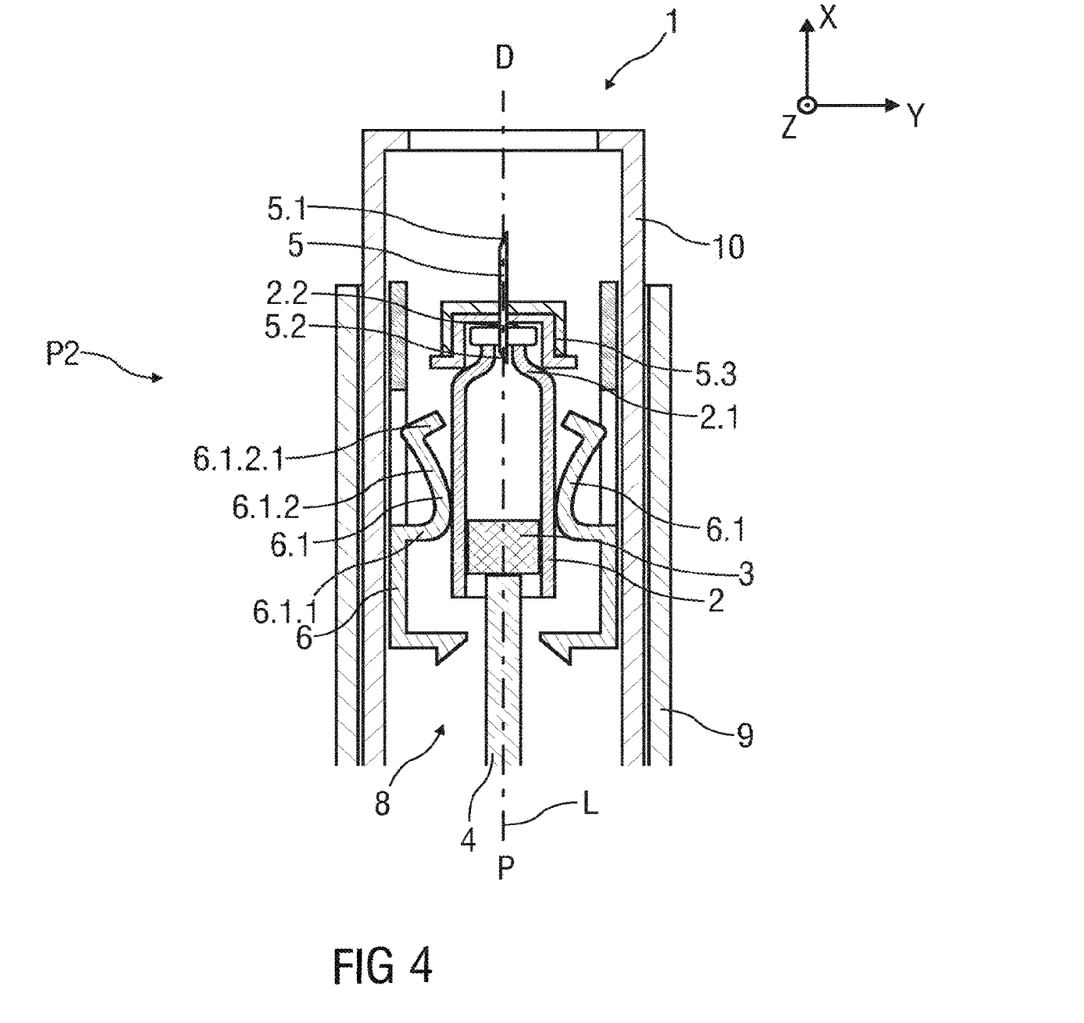
FIG. 4 is a schematic longitudinal section view of an alternative embodiment of a medicament delivery device in an operating position.

FIGS. 3 and 4 show an alternative embodiment of the medicament delivery device 1, whereby the drive element 8 is realized by the piston rod 4. Thereby, FIG. 3 shows the medicament delivery device 1 in the initial position P1 and FIG. 4 shows the medicament delivery device 1 in the operating position P2.

The piston rod 4 may be coupled to a button for an automatic medicament delivery or the piston rod 4 will be controlled manually by applying a manual force on the piston rod 4. When the piston rod 4 moves into the distal direction D, the piston rod 4 engages with the bung 3. Moving the piston rod 4 further into the distal direction D causes a distal movement of the cartridge 2, because the force required to move the cartridge 2 in the distal direction D is smaller than the force required to move the bung 3 with respect to the cartridge 2 in the distal direction D.

When the cartridge 2 is pushed in the distal direction D by the piston rod 4, the cartridge 2 is held in position only by the cartridge carrier 6. In particular, when the needle cap 7 is removed, the sealing element 2.2 will not be pierced immediately, but only when the piston rod 4 is moved distally. Thus, a so-called wet injection may be avoided. Due to the distal movement of the cartridge 2 against the resilient arms 6.1, the resilient arms 6.1 deform radially outwards into the recesses of the cartridge carrier 6. Thus, the cartridge 2 moves in the distal direction D with respect to the cartridge carrier 6 and the sleeve 10 until it abuts against the needle thread 5.3, whereby the needle tip of the inner needle section 5.2 pierces the sealing element 2.2 of the cartridge 2. Now, the injection needle 5 is in fluid communication with the medicament, but still covered by the sleeve 10 as it is shown in FIG. 4.

Moreover, an area of the injection needle 5 may be sealed against environmental influences according to regulatory requirements for medicament combination products.

Figure 5:
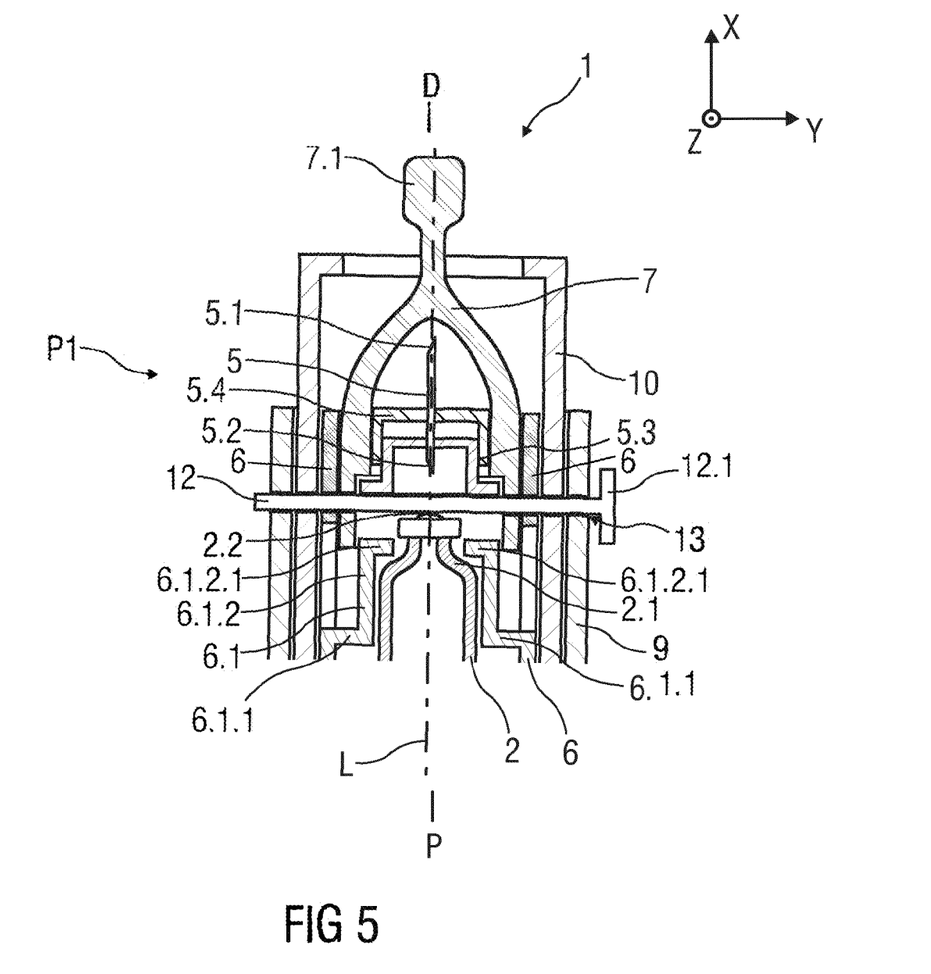
FIG. 5 is a schematic longitudinal section of another exemplary embodiment of a medicament delivery device having a removable sealing part.
Figure 6:
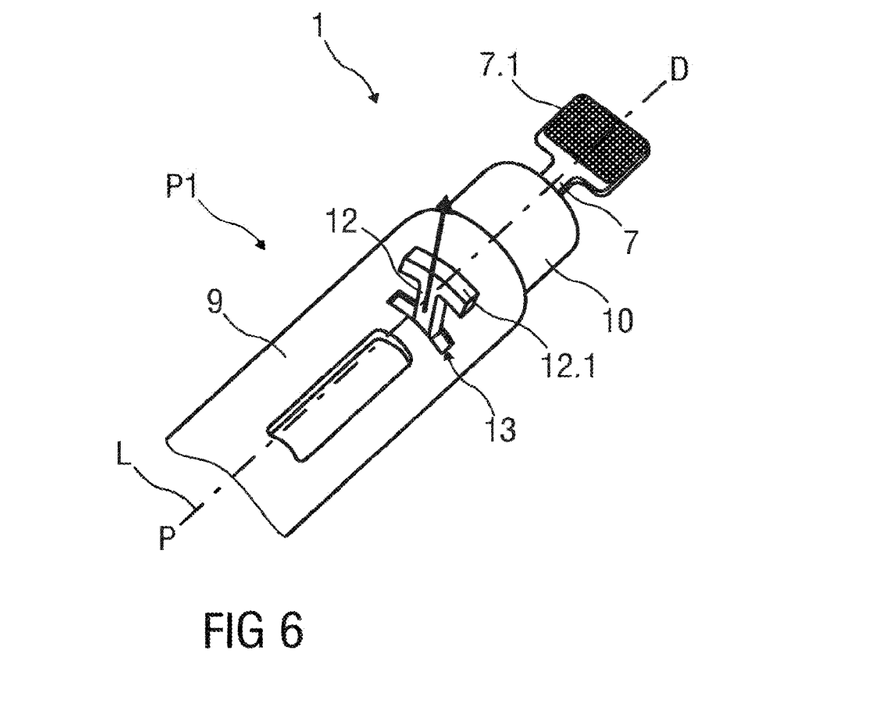
FIG. 6 is a schematic perspective view of the embodiment of FIG. 5.

FIG. 5 is a schematic longitudinal section of another exemplary embodiment of a medicament delivery device 1 having a removable sealing part 12. FIG. 6 is a schematic perspective view of the embodiment of FIG. 5.

The medicament delivery device 1 is substantially identical with the medicament delivery device of FIGS. 1 and 2. In addition to the features of this medicament delivery device 1, a sealing part 12 having the shape of a tab or strip is arrangeable transversally within the medicament delivery device 1 through a respective opening 13 transversally, at a substantially right angle, arranged with respect to the longitudinal axis L. The opening 13 extends through the outer body 9, the sleeve 10, the needle cap 7 and the cartridge carrier 6, if applicable. In the initial position P1, the sealing part 12 is located within the opening 13 distally from the sealing element 2.2 of the cartridge 2 and proximally from the inner needle section 5.2 and from the needle thread 5.3, which is arranged on a needle hub 5.4. Due to the sealing part 12 being arranged within the opening 13, the needle cap 7 cannot be removed, the sleeve 10 cannot be depressed and the cartridge 2 cannot be advanced prior to removal of the sealing part 12. The cartridge 2 may be biased by the drive element (not illustrated) in the distal direction D thereby pushing the sealing part 12 against the needle hub 5.4 for sealing the inner needle section 5.2. The sealing part 12 may be arranged to sterilely seal the inner needle section 5.2. In an exemplary embodiment, a width of the strip-shaped sealing part 12 is at least as great as a diameter of the needle hub 5.4. One end of the sealing part 12 may comprise a handle 12.1 for facilitating removal. The handle 12.1 may be arranged as a T-shaped bar.

In order to allow operation of the medicament delivery device 1, a user may grip the sealing part 12, e.g. by the handle 12.1, and pull it out of the opening 13. The medicament delivery device 1 may then be operated as described above in the embodiments of FIGS. 1 and 2. The sealing part 12 may likewise be combined with a medicament delivery device 1 as illustrated in FIGS. 3 and 4.

Figure 7:
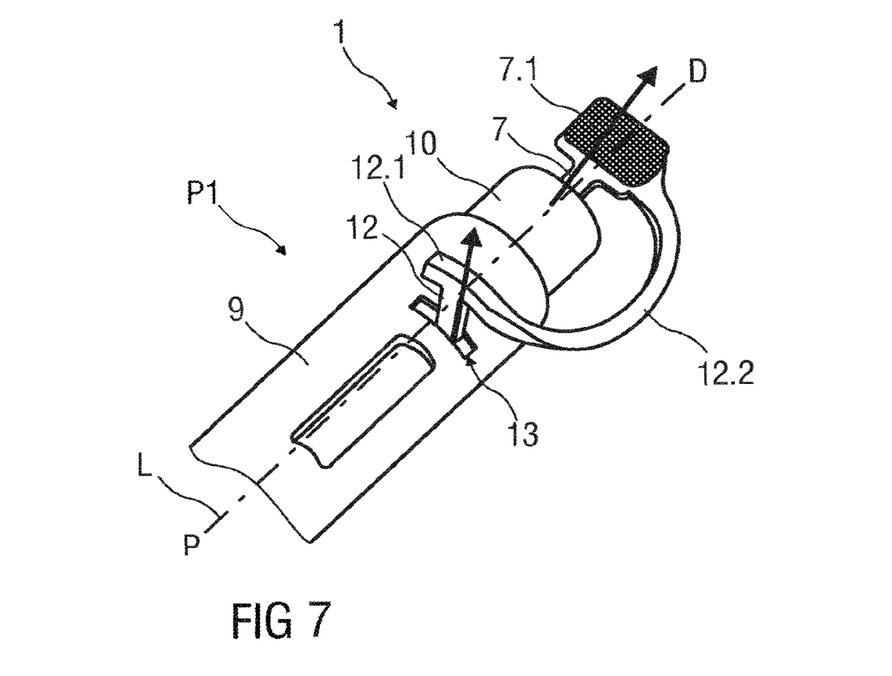
FIG. 7 is a schematic perspective view of another exemplary embodiment of a medicament delivery device having a removable sealing part connected to a removal aid of a needle cap.

FIG. 7 is a schematic perspective view of another exemplary embodiment of a medicament delivery device 1. The medicament delivery device 1 is substantially identical with the medicament delivery device of FIGS. 5 and 6. In addition to the features of this medicament delivery device 1, the sealing part 12 is connected by a flexible strip 12.2 to the cap 7. In particular, the strip 12.2 may connect the handle 12.1 to the removal aid 7.1. In an exemplary embodiment, the cap 7 and the sealing part 12 are integrally shaped.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Trp(O2)25, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present disclosure, which encompass such modifications and any and all equivalents thereof.

LIST OF REFERENCES 1 medicament delivery device
2 cartridge
2.1 shoulder
2.2 sealing element
3 bung
4 piston rod
5 injection needle 5.1 outer needle section
5.2 inner needle section
5.3 needle thread
5.4 needle hub
6 cartridge carrier
6.1 resilient arm
6.1.1 first section
6.1.2 second section
6.1.2.1 hook end
7 needle cap
7.1 removal aid
8 drive element
9 outer body
10 sleeve
11 spring unit
12 sealing part
12.1 handle
12.2 strip
13 opening
D distal direction
L longitudinal axis
P proximal direction
P1 initial position
P2 operating position
x, y, z cartesian coordinates

The invention claimed is:

1. A medicament delivery device comprising:
a housing;
a medicament cartridge contained in the housing such that (i) a distal end of the housing is distal to a distal end of the medicament cartridge, (ii) a proximal end of the housing is proximal to a proximal end of the medicament cartridge, and (iii) the housing extends an entire length of the medicament cartridge, the proximal end of the medicament cartridge defining a proximal opening, the distal end of the medicament cartridge defining a distal opening, and a sealing element covering the distal opening;
a hollow needle attached to a needle holder within the housing, the hollow needle having a proximal end and a distal end, the proximal end of the hollow needle, in an initial position, being distally spaced from the sealing element covering the distal opening of the medicament cartridge such that the hollow needle is not in fluid communication with medicament in the medicament cartridge;
a member disposed within the housing, the member comprising (i) a sidewall extending substantially parallel to a sidewall of the housing and (ii) a distal portion extending inward towards a longitudinal axis of the housing;
a piston drive member configured to be advanced within the medicament cartridge;
a piston disposed within the medicament cartridge and configured to seal the proximal end of the medicament cartridge; and
a removable needle cover configured to be secured with respect to the housing, the removable needle cover, when secured with respect to the housing, having a first portion that protrudes from the housing and a second portion that is slidably engaged with the member,
wherein the removable needle cover is configured such that removal of the removable needle cover from the housing causes the second portion of the removable needle cover to disengage from the member thereby permitting the member to be moved relative to the medicament cartridge to place the hollow needle in fluid communication with the medicament in the medicament cartridge.

2. The medicament delivery device of claim 1, further comprising a spring configured to cause relative axial movement between the medicament cartridge and the member.

3. The medicament delivery device of claim 2, wherein the spring is configured to distally bias the medicament cartridge relative to the member.

4. The medicament delivery device of claim 2, wherein the spring is configured to distally bias the medicament cartridge relative to the housing.

5. The medicament delivery device of claim 2, wherein the removable needle cover is configured such that the removal of the removable needle cover from the housing releases the spring, thereby causing the relative axial movement between the medicament cartridge and the member.

6. The medicament delivery device of claim 1, further comprising a trigger element configured such that actuation of the trigger element causes (i) relative movement between the medicament cartridge and the member and (ii) the hollow needle to be placed in fluid communication with the medicament in the medicament cartridge.

7. The medicament delivery device of claim 6, wherein the trigger element is configured such that the actuation of the trigger element releases a spring to cause the relative movement between the medicament cartridge and the member.

8. The medicament delivery device of claim 6, wherein the trigger element is configured such that the actuation of the trigger element causes the medicament cartridge to move axially relative to the housing.

9. The medicament delivery device of claim 6, wherein the trigger element is configured such that the actuation of the trigger element further causes the piston drive member to be advanced within the medicament cartridge to dispense the medicament in the medicament cartridge through the hollow needle after the hollow needle has been placed in fluid communication with the medicament in the medicament cartridge.

10. The medicament delivery device of claim 6, wherein the removable needle cover, when secured with respect to the housing, is configured to prevent the trigger element from being actuated.

11. The medicament delivery device of claim 1, wherein the medicament cartridge comprises a cylindrical body defining a chamber for containing the medicament.

12. The medicament delivery device of claim 11, wherein the medicament cartridge comprises the piston disposed in the chamber.

13. The medicament delivery device of claim 12, wherein the piston seals the proximal opening of the medicament cartridge such that the medicament is contained in the chamber between the piston and the sealing element.

14. The medicament delivery device of claim 1, wherein the hollow needle is aligned with an opening in the housing.

15. The medicament delivery device of claim 1, wherein the second portion of the removable needle cover engages the member to prevent the member from moving relative to the medicament cartridge when the removable needle cover is fixed with respect to the housing.

16. The medicament delivery device of claim 1, wherein the second portion of the removable needle cover engages the member to prevent the member from moving axially relative to the medicament cartridge when the removable needle cover is fixed with respect to the housing.

17. The medicament delivery device of claim 1, wherein the removable needle cover is configured to prevent relative axial movement between the hollow needle and the medicament cartridge when the removable needle cover is fixed with respect to the housing.

18. The medicament delivery device of claim 1, wherein the removable needle cover is configured such that the removal of the removable needle cover from the housing causes the hollow needle to move relative to the medicament cartridge.

19. The medicament delivery device of claim 18, wherein the removable needle cover is configured such that the removal of the removable needle cover from the housing causes the hollow needle to pierce the sealing element of the medicament cartridge.

20. The medicament delivery device of claim 1, wherein the removable needle cover is configured to cover an opening of the medicament delivery device when the removable needle cover is secured with respect to the housing.

21. The medicament delivery device of claim 1, wherein the removable needle cover conceals the hollow needle when the removable needle cover is secured with respect to the housing.

22. The medicament delivery device of claim 1, wherein the member comprises at least one arm configured to control axial movement of the medicament cartridge.

23. The medicament delivery device of claim 1, wherein the housing and the member are distinct components of the medicament delivery device.

24. The medicament delivery device of claim 1, wherein at least a portion of the member is movable relative to the housing.

25. The medicament delivery device of claim 1, wherein the member is axially movable relative to the medicament cartridge.

26. The medicament delivery device of claim 1, wherein the slidable engagement between the second portion of the removable needle cover and the member comprises a direct engagement.

27. A medicament delivery device comprising:
a housing configured to contain a medicament cartridge such that (i) a distal end of the housing is distal to a distal end of the medicament cartridge, (ii) a proximal end of the housing is proximal to a proximal end of the medicament cartridge, and (iii) the housing extends an entire length of the medicament cartridge when the medicament cartridge is in the housing;
a hollow needle attached to a needle holder within the housing, the hollow needle having a proximal end and a distal end, the proximal end of the hollow needle, in an initial position, being distally spaced from a sealing element at the distal end of the medicament cartridge when the medicament cartridge is contained in the housing such that the hollow needle is not in fluid communication with medicament in the medicament cartridge;
a member disposed within the housing, the member comprising (i) a sidewall extending substantially parallel to a sidewall of the housing and (ii) a distal portion extending inward towards a longitudinal axis of the housing;
a piston drive member configured to be advanced within the medicament cartridge when the medicament cartridge is contained in the housing;
a piston disposed within the medicament cartridge and configured to seal the proximal end of the medicament cartridge; and
a removable needle cover configured to be secured with respect to the housing, the removable needle cover, when secured with respect to the housing, having a first portion that protrudes from the housing and a second portion that is slidably engaged with the member,
wherein the removable needle cover is configured such that removal of the removable needle cover from the housing causes the second portion of the removable needle cover to disengage from the member thereby permitting the member to be moved relative to the medicament cartridge to place the hollow needle in fluid communication with the medicament in the medicament cartridge when the medicament cartridge is contained in the housing.

28. The medicament delivery device of claim 27, comprising the medicament cartridge contained in the housing.

29. The medicament delivery device of claim 28, wherein the medicament cartridge contains the medicament.

* * * * *